(12) United States Patent
Nazzaro

(10) Patent No.: US 10,695,485 B2
(45) Date of Patent: Jun. 30, 2020

(54) VERY HIGH VOLUME USER FILLED DRUG DELIVERY DEVICE

(71) Applicant: Insulet Corporation, Billerica, MA (US)

(72) Inventor: David Nazzaro, Groveland, MA (US)

(73) Assignee: Insulet Corporation, Acton, MA (US)

( * ) Notice: Subject to any disclaimer, the term of this patent is extended or adjusted under 35 U.S.C. 154(b) by 30 days.

(21) Appl. No.: 15/912,923

(22) Filed: Mar. 6, 2018

(65) Prior Publication Data

US 2018/0256815 A1    Sep. 13, 2018

Related U.S. Application Data

(60) Provisional application No. 62/468,152, filed on Mar. 7, 2017.

(51) Int. Cl.
*A61M 5/145* (2006.01)
*A61M 5/158* (2006.01)
(Continued)

(52) U.S. Cl.
CPC ........ *A61M 5/1454* (2013.01); *A61M 5/1408* (2013.01); *A61M 5/14248* (2013.01); *A61M 5/158* (2013.01)

(58) Field of Classification Search
CPC .............. A61M 5/1454; A61M 5/1408; A61M 5/14248; A61M 5/158; A61M 5/14244;
(Continued)

(56) References Cited

U.S. PATENT DOCUMENTS

| 1,441,508 A | 1/1923 | Marius et al. |
| 2,198,666 A | 4/1940 | Gruskin |

(Continued)

FOREIGN PATENT DOCUMENTS

| CA | 606281 A | 10/1960 |
| DE | 4200595 A1 | 7/1993 |

(Continued)

OTHER PUBLICATIONS

Lind, et al.,"Linear Motion Miniature Actuators." Paper presented at the 2nd Tampere International Conference on Machine Automation, Tampere, Finland (Sep. 15-18, 1998) 2 pages.
(Continued)

*Primary Examiner* — Kami A Bosworth
*Assistant Examiner* — Antarius S Daniel

(57) ABSTRACT

A wearable drug delivery device that can deliver high volumes of liquid drugs stored in one or more corresponding containers to a patient is provided. The wearable drug delivery device can include first and second containers to store first and second liquid drugs, respectively. A first set of energy transfer spheres can be coupled to a first spring and a first plunger positioned within the first container. A second set of energy transfer spheres can be coupled to a second spring and a second plunger positioned within the second container. The first spring can expand to advance the first set of energy transfer spheres and the first plunger to expel the first liquid drug for delivery to the patient. The second spring can expand to advance the second set of energy transfer spheres and the second plunger to expel the second liquid drug for delivery to the patient.

20 Claims, 9 Drawing Sheets

(51) Int. Cl.
*A61M 5/14* (2006.01)
*A61M 5/142* (2006.01)

(58) Field of Classification Search
CPC .. A61M 5/19; A61M 5/16827; A61M 5/2448; A61M 5/284; A61M 5/31596; A61M 2005/14268; A61M 2005/14252; A61M 2005/14506; A61M 2005/31518; A61M 5/1407; A61M 5/31578; A61M 2005/31516
See application file for complete search history.

(56) References Cited

U.S. PATENT DOCUMENTS

| | | | |
|---|---|---|---|
| 3,885,662 A | 5/1975 | Schaefer | |
| 3,946,732 A | 3/1976 | Hurscham | |
| 4,108,177 A | 8/1978 | Pistor | |
| 4,268,150 A | 5/1981 | Chen | |
| 4,313,439 A * | 2/1982 | Babb | A61M 5/1454 128/DIG. 12 |
| 4,424,720 A | 1/1984 | Bucchianeri | |
| 4,435,173 A | 3/1984 | Siposs et al. | |
| 4,498,843 A | 2/1985 | Schneider et al. | |
| 4,507,115 A | 3/1985 | Kambara et al. | |
| 4,551,134 A | 11/1985 | Slavik et al. | |
| 4,562,751 A | 1/1986 | Nason et al. | |
| 4,585,439 A | 4/1986 | Michel | |
| 4,601,707 A | 7/1986 | Albisser et al. | |
| 4,634,427 A | 1/1987 | Hannula et al. | |
| 4,671,429 A | 6/1987 | Spaanderman et al. | |
| 4,678,408 A | 7/1987 | Nason et al. | |
| 4,684,368 A | 8/1987 | Kenyon | |
| 4,755,169 A | 7/1988 | Sarnoff et al. | |
| 4,846,797 A * | 7/1989 | Howson | A61M 5/1456 604/154 |
| 4,898,579 A | 2/1990 | Groshong et al. | |
| 4,944,659 A | 7/1990 | Labbe et al. | |
| 4,969,874 A | 11/1990 | Michel et al. | |
| 5,007,458 A | 4/1991 | Marcus et al. | |
| 5,062,841 A | 11/1991 | Siegel | |
| 5,205,819 A | 4/1993 | Ross et al. | |
| 5,213,483 A | 5/1993 | Flaherty et al. | |
| 5,261,882 A | 11/1993 | Sealfon | |
| 5,277,338 A | 1/1994 | Divall | |
| 5,281,202 A | 1/1994 | Weber et al. | |
| 5,346,476 A | 9/1994 | Elson | |
| 5,364,342 A | 11/1994 | Beuchat et al. | |
| 5,433,710 A | 7/1995 | VanAntwerp et al. | |
| 5,582,593 A | 12/1996 | Hultman | |
| 5,637,095 A | 6/1997 | Nason et al. | |
| 5,665,070 A | 9/1997 | McPhee | |
| 5,713,875 A | 2/1998 | Tanner, II | |
| 5,747,350 A | 5/1998 | Sattler | |
| 5,748,827 A | 5/1998 | Holl et al. | |
| 5,776,103 A | 7/1998 | Kriesel et al. | |
| 5,779,676 A | 7/1998 | Kriesel et al. | |
| 5,785,688 A | 7/1998 | Joshi et al. | |
| 5,797,881 A | 8/1998 | Gadot | |
| 5,800,397 A | 9/1998 | Wilson et al. | |
| 5,807,075 A | 9/1998 | Jacobsen et al. | |
| 5,839,467 A | 11/1998 | Saaski et al. | |
| 5,891,097 A | 4/1999 | Saito et al. | |
| 5,897,530 A | 4/1999 | Jackson | |
| 5,906,597 A | 5/1999 | McPhee | |
| 5,911,716 A | 6/1999 | Rake et al. | |
| 5,919,167 A | 7/1999 | Mulhauser et al. | |
| 5,957,890 A | 9/1999 | Mann et al. | |
| 5,961,492 A | 10/1999 | Kriesel et al. | |
| 6,019,747 A | 2/2000 | McPhee | |
| 6,174,300 B1 | 1/2001 | Kriesel et al. | |
| 6,190,359 B1 | 2/2001 | Heruth | |
| 6,200,293 B1 | 3/2001 | Kriesel et al. | |
| 6,363,609 B1 | 4/2002 | Pickren | |
| 6,375,638 B2 | 4/2002 | Nason et al. | |
| 6,474,219 B2 | 11/2002 | Klitmose et al. | |
| 6,485,461 B1 | 11/2002 | Mason et al. | |
| 6,485,462 B1 | 11/2002 | Kriesel | |
| 6,488,652 B1 | 12/2002 | Weijand et al. | |
| 6,520,936 B1 | 2/2003 | Mann | |
| 6,527,744 B1 | 3/2003 | Kriesel et al. | |
| 6,537,249 B2 | 3/2003 | Kriesell et al. | |
| 6,569,115 B1 | 5/2003 | Barker et al. | |
| 6,595,956 B1 | 7/2003 | Gross et al. | |
| 6,656,158 B2 | 12/2003 | Mahoney et al. | |
| 6,699,218 B2 | 3/2004 | Flaherty et al. | |
| 6,723,072 B2 | 4/2004 | Flaherty et al. | |
| 6,851,260 B2 | 2/2005 | Mernoe | |
| 6,883,778 B1 | 4/2005 | Newton et al. | |
| 7,144,384 B2 * | 12/2006 | Gorman | A61M 5/14276 604/131 |
| 7,160,272 B1 | 1/2007 | Eyal et al. | |
| 7,771,392 B2 | 8/2010 | De Polo et al. | |
| 7,914,499 B2 * | 3/2011 | Gonnelli | A61M 5/14526 604/186 |
| 8,382,703 B1 * | 2/2013 | Abdelaal | A61M 5/14216 604/152 |
| 8,499,913 B2 | 8/2013 | Gunter | |
| 8,939,935 B2 | 1/2015 | O'Connor et al. | |
| 9,180,244 B2 | 11/2015 | Anderson et al. | |
| 9,192,716 B2 | 11/2015 | Jugl et al. | |
| 9,402,950 B2 | 8/2016 | Dilanni et al. | |
| 2001/0056258 A1 | 12/2001 | Evans | |
| 2002/0029018 A1 | 3/2002 | Jeffrey | |
| 2002/0173769 A1 | 11/2002 | Gray et al. | |
| 2003/0040715 A1 | 2/2003 | D'Antonio et al. | |
| 2003/0109827 A1 | 6/2003 | Lavi et al. | |
| 2004/0064088 A1 | 4/2004 | Gorman et al. | |
| 2004/0068224 A1 | 4/2004 | Couvillon et al. | |
| 2004/0069044 A1 | 4/2004 | Lavi et al. | |
| 2004/0153032 A1 | 8/2004 | Garribotto et al. | |
| 2005/0020980 A1 | 1/2005 | Inoue et al. | |
| 2005/0203461 A1 | 9/2005 | Flaherty et al. | |
| 2005/0238507 A1 | 10/2005 | Dilanni et al. | |
| 2005/0273059 A1 | 12/2005 | Mernoe et al. | |
| 2006/0041229 A1 | 2/2006 | Garibotto et al. | |
| 2006/0079765 A1 | 4/2006 | Neer et al. | |
| 2006/0173439 A1 | 8/2006 | Thorne et al. | |
| 2006/0178633 A1 | 8/2006 | Garibotto et al. | |
| 2008/0114304 A1 | 5/2008 | Nalesso et al. | |
| 2008/0172028 A1 | 7/2008 | Blomquist | |
| 2009/0024083 A1 * | 1/2009 | Kriesel | A61M 5/14244 604/86 |
| 2010/0036326 A1 | 2/2010 | Matusch | |
| 2010/0241066 A1 | 9/2010 | Hansen et al. | |
| 2011/0144586 A1 | 6/2011 | Michaud et al. | |
| 2013/0006213 A1 | 1/2013 | Arnitz et al. | |
| 2013/0017099 A1 | 1/2013 | Genoud et al. | |
| 2013/0064701 A1 | 3/2013 | Konishi | |
| 2013/0245545 A1 | 9/2013 | Arnold et al. | |
| 2013/0267932 A1 | 10/2013 | Franke et al. | |
| 2014/0018730 A1 | 1/2014 | Muller-Pathle | |
| 2014/0142508 A1 | 5/2014 | Dilanni et al. | |
| 2014/0148784 A1 | 5/2014 | Anderson et al. | |
| 2014/0171901 A1 | 6/2014 | Langsdorf et al. | |
| 2015/0041498 A1 | 2/2015 | Kakiuchi et al. | |
| 2015/0057613 A1 | 2/2015 | Clemente et al. | |
| 2015/0202386 A1 | 7/2015 | Brady et al. | |
| 2015/0290389 A1 | 10/2015 | Nessel | |
| 2015/0297825 A1 | 10/2015 | Focht et al. | |
| 2016/0025544 A1 | 1/2016 | Kamen | |
| 2016/0193423 A1 | 7/2016 | Bilton | |
| 2017/0021096 A1 | 1/2017 | Cole et al. | |
| 2017/0021137 A1 | 1/2017 | Cole | |
| 2017/0216516 A1 | 8/2017 | Dale et al. | |
| 2017/0239415 A1 | 8/2017 | Hwang et al. | |
| 2018/0313346 A1 | 11/2018 | Oakes et al. | |

FOREIGN PATENT DOCUMENTS

| | | |
|---|---|---|
| EP | 0867196 A2 | 9/1998 |
| EP | 1177802 A1 | 2/2002 |
| EP | 2468338 A1 | 6/2012 |

(56) References Cited

FOREIGN PATENT DOCUMENTS

| | | |
|---|---|---|
| EP | 2703024 A1 | 3/2014 |
| FR | 2096275 A5 | 2/1972 |
| FR | 2455269 A1 | 11/1980 |
| GB | 357139 A | 9/1931 |
| GB | 810488 A | 3/1959 |
| GB | 2549750 A | 11/2017 |
| IL | 46017 A | 11/1977 |
| JP | H08238324 A | 9/1996 |
| NL | 1019126 C1 | 4/2003 |
| WO | 8101658 A1 | 6/1981 |
| WO | 8606796 A1 | 11/1986 |
| WO | 9855073 A1 | 12/1998 |
| WO | 9910040 A1 | 3/1999 |
| WO | 9910049 A1 | 3/1999 |
| WO | 9962576 A1 | 12/1999 |
| WO | 200178812 A1 | 10/2001 |
| WO | 200226282 A2 | 4/2002 |
| WO | 2002076535 A1 | 10/2002 |
| WO | 2003097133 A1 | 11/2003 |
| WO | 2004056412 A2 | 7/2004 |
| WO | 2007066152 A2 | 6/2007 |
| WO | 2009039203 A2 | 3/2009 |
| WO | 2010139793 A1 | 12/2010 |
| WO | 2011075042 A1 | 6/2011 |
| WO | 2011133823 A1 | 6/2011 |
| WO | 2012073032 A1 | 6/2012 |
| WO | 2013050535 A2 | 4/2013 |
| WO | 2013137893 A1 | 9/2013 |
| WO | 2014149357 A1 | 9/2014 |
| WO | 2015032772 A1 | 3/2015 |
| WO | 2015081337 A2 | 6/2015 |
| WO | 2015117854 A1 | 8/2015 |
| WO | 2015167201 A1 | 11/2015 |
| WO | 2015177082 A1 | 11/2015 |
| WO | 2017187177 A1 | 11/2017 |

OTHER PUBLICATIONS

Author unknown, "The Animas R-1000 Insulin Pump—Animas Corporation intends to exit the insulin pump business and discontinue the manufacturing and sale of Animas® Vibe® and OneTouch Ping® insulin pumps." [online], Dec. 1999 [retrieved on Oct. 16, 2018]. Retrieved from the Internet URL: http://www.animaspatientsupport.com/.

Author unknown, CeramTec "Discover the Electro Ceramic Products CeramTec acquired from Morgan Advanced Materials" [online], Mar. 1, 2001 [retrieved on Oct. 17, 2018]. Retrieved from the Internet URL: http://www.morgantechnicalceramics.com/, 2 pages.

Vaughan, M.E., "The Design, Fabrication, and Modeling of a Piezoelectric Linear Motor." Master's thesis, Virginia Polytechnic Institute and State University, VA. (2001).

Galante, et al., "Design, Modeling, and Performance of a High Force Piezoelectric Inchworm Motor," Journal of ntelligent Material Systems and Structures, vol. 10, 962-972 (1999).

International Search Report and Written Opinion for application No. PCT/US2017/034811, dated Oct. 18, 2017, 15 pages.

International Search Report and Written Opinion for application No. PCT/US17/46508 dated Jan. 17, 2018, 14 pages.

International Search Report and Written Opinion for application No. PCT/US17/46777, dated Dec. 13, 2017, 14 pages.

International Search Report and Written Opinion for application No. PCT/US17/46737, dated Dec. 14, 2017, 11 pages.

International Search Report and Written Opinion for application No. PCT/US17/55054, dated Jan. 25, 2018, 13 pages.

International Search Report and Written Opinion for application No. PCT/US2018/014351, dated Jun. 4, 2018, 11 pages.

International Search Report and Written Opinion for application No. PCT/US18/45155, dated Oct. 15, 2018, 15 pages.

International Search Report and Written Opinion for application No. PCT/US17/34814, dated Oct. 11, 2017, 16 pages.

International Search Report and Written Opinion for International application No. PCT/US2019/035756, dated Jul. 31, 2019, 10 pages.

Extended European Search Report for the European Patent Application No. EP19177571, dated Oct. 30, 2019, 8 pages.

International Search Report and Written Opinion for the International Patent Application No. PCT/US2019/063615, dated May 3, 2020, 17 pages.

International Preliminary Report on Patentability for the International Patent Application No. PCT/US2018/045155, dated Feb. 13, 2020, 10 pages.

\* cited by examiner

VERY HIGH VOLUME USER FILLED DRUG DELIVERY DEVICE

CROSS-REFERENCE TO RELATED APPLICATIONS

This application claims the benefit of U.S. Provisional Application No. 62/468,152, filed Mar. 7, 2017, which is incorporated herein by reference in its entirety.

TECHNICAL FIELD

Embodiments generally relate to medication delivery. More particularly, embodiments relate to wearable drug delivery devices.

BACKGROUND

Many conventional drug delivery devices that are wearable are limited to only delivering small volumes of a liquid drug to a patient. Other conventional drug delivery devices that can store and deliver larger volumes of a liquid drug to a patient are not designed to be wearable and so are bulky, cumbersome, and uncomfortable when attempted to be worn by a patient. Further, many of these conventional drug delivery devices are not fillable by the patient, thereby limiting their usefulness and longevity.

A need therefore exists for a more compact and lightweight wearable drug delivery device for providing relatively high volumes of a liquid drug to a patient that can be filled by the patient and worn in a comfortable manner.

DETAILED DESCRIPTION

This disclosure presents various systems, components, and methods for delivering a liquid drug or medicine to a patient or user. Each of the systems, components, and methods disclosed herein provides one or more advantages over conventional systems, components, and methods.

Various embodiments include a wearable drug delivery device that can deliver high volumes of one or more liquid drugs stored in one or more corresponding containers to a patient or user. The wearable drug delivery device can include a first container to store a first liquid drug and a second container to store a second liquid drug. A first set of energy transfer spheres can be coupled to a first spring and a first plunger positioned within the first container. A second set of energy transfer spheres can be coupled to a second spring and a second plunger positioned within the second container. The first spring can expand to advance the first set of energy transfer spheres toward the first plunger to advance the first plunger further into the first cartridge, thereby expelling a portion of the first liquid drug from the first container for delivery to the patient. The second spring can expand to advance the second set of energy transfer spheres toward the second plunger to advance the second plunger further into the second cartridge, thereby expelling a portion of the second liquid drug from the second container for delivery to the patient. The first and second liquid drugs can be the same drug or can be different drugs. The first and second drugs can be delivered in succession or can be mixed for delivery to the patient. The wearable drug delivery device can be filled or refilled by the patient. Other embodiments are disclosed and described.

Figure 1:
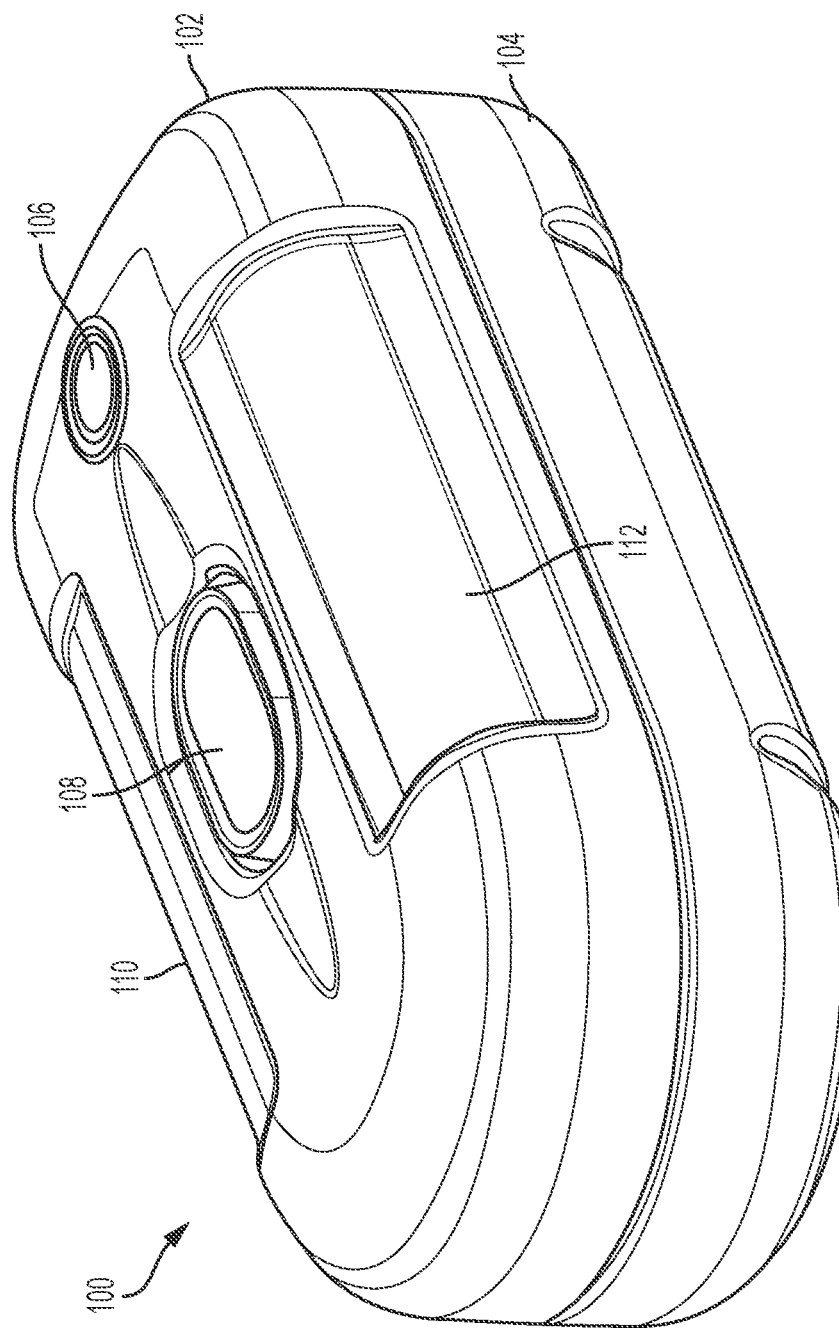
FIG. 1 illustrates an exemplary drug delivery device.

FIG. 1 illustrates an exemplary embodiment of a drug delivery device 100. The drug delivery device 100 can include a top portion or cover 102 and a lower portion or base 104. The top portion 102 and the lower portion 104 can together form a housing of the drug delivery device 100. The top portion 102 and the lower portion 104 can be coupled together to form an outside portion of the drug delivery device 100. The top portion 102 and the lower portion 104 can be formed from any material including, for example, plastic, metal, rubber, or any combination thereof.

The drug delivery device 100 can be used to deliver one or more therapeutic agents (e.g., one or more drugs) to a patient or user. In various embodiments, the drug delivery device 100 can include two or more containers for retaining or storing liquid drugs. The liquid drugs can be the same liquid drug or can be different liquid drugs. The drug delivery device 100 can be used to deliver the liquid drugs from the containers to the patient. Any type of liquid drug can be stored by the drug delivery device 100 and delivered to the patient. In various embodiments, the containers can contain any therapeutic agent such as, for example, a drug, a subcutaneous injectable, a medicine, or a biologic, or any combination thereof. The liquid drugs stored by the drug delivery device 100 can be delivered in succession or can be combined for delivery to the patient. A patient receiving a drug or other medicine (or any liquid) from the drug delivery device 100 can also be referred to as a user.

The drug delivery device 100 can provide any amount of the stored liquid drugs to a patient over any period of time. In various embodiments, the drug delivery device 100 can provide the stored liquid drugs to the patient in a single dose over a desired amount of time. In various embodiments, the drug delivery device 100 can provide the stored liquid drugs to the patient over multiple doses. Each of the multiple doses can include substantially the same amount of the liquid drug or drugs or the sizes of the doses can vary. Further, each of the multiple doses can be provided to the patient over substantially the same amount of time or the delivery times can vary. Additionally, the amount of time between multiple doses can be approximately equal or can vary.

The drug delivery device 100 can maintain the liquid drugs within two or more primary drug containers. For purposes of explanation and illustration herein, the drug delivery device 100 is described as having two primary drug containers but is not so limited. The primary drug containers can each be a cartridge. As an example, each cartridge can be an International Organization for Standardization (ISO)

standardized cartridge. The drug delivery device 100 can be provided to the patient with preloaded and prefilled cartridges. In various embodiments, the drug delivery device 100 can include a slot or opening for a patient to load prefilled cartridges into the drug delivery device 100. In various embodiments, the drug delivery device 100 can be designed and/or intended for a single use such that after the liquid drugs are delivered to the patient, the drug delivery device 100 can be discarded.

In various embodiments, the primary drug containers can be filled or refilled by a patient such that the drug delivery device 100 can be reused. In various embodiments, the drug delivery device 100 can include a port for accessing and filling the primary drug containers. As an example, the drug delivery device 100 can include a fill port 106. The fill port 106 can provide access to each of the drug containers contained within the drug delivery device 100 such that a user can fill each drug container through the fill port 106. Since the fill port 106 provides access to each drug container within the drug delivery device 100, the fill port 106 can be considered a unionized fill port.

As shown in FIG. 1, the top portion 102 can include a patient interaction element or component 108. In various embodiments, the patient interaction element 108 can be a push button or other patient input device. The patient interaction element 108 can be used to activate the drug delivery device 100. For example, when a patient presses on the patient interaction element 108, the drug delivery device 100 can begin delivering the stored liquid drugs to the patient. Prior to activation, the drug delivery device 100 can remain in an idle state of operation. In various embodiments, the patient interaction element 108 can be used to start, stop, and/or restart delivery of the liquid drugs to the patient to enable a patient to dispense multiple doses of one or more liquid drugs.

The drug delivery device 100 can be a wearable drug delivery device 100. As a wearable device, the drug delivery device 100 can be an on-body delivery system (OBDS) or a portion thereof. The drug delivery device 100 can be coupled to a patient in many ways. For example, the lower portion 104 of the drug delivery device 100 can include an adhesive for attaching to a patient. In various embodiments, the drug delivery device 100 can be attached to a secondary device attached or worn by the patient such that the drug delivery device 100 fits onto or can be coupled to the secondary device.

FIG. 1 illustrates an exemplary form factor of the drug delivery device 100. In various embodiments, the drug delivery device 100 can be designed according to any desired form factor—for example, according to any desired shape and size of the top and lower portions 102 and 104. Further, the drug delivery device 100 can include any number of components that can be coupled together to form the housing of the drug delivery device 100.

In various embodiments, the drug delivery device 100 can be a relatively high capacity drug delivery device capable of relativity fast delivery of liquids with relativity high viscosities. In various embodiments, the drug delivery device 100 can include two 5 mL drug cartridges (e.g., two 5 mL ISO drug containers) such that the drug delivery device 100 can store and deliver at least 10 mL of one or more liquid drugs to a user. Accordingly, the drug delivery device 100 can be considered to be a very high volume (VHV) (e.g., 10 mL or more) drug delivery device.

The drug delivery device 100 can include a first opening or window 110 and a second opening or window 112. The windows 110 and 112 can expose a portion of each drug container (e.g., each cartridge) positioned within the drug delivery device 100. In various embodiments, the window 110 can be positioned adjacent to a first 5 mL drug cartridge and the window 112 can be positioned adjacent to a second 5 mL drug cartridge. The windows 110 and 112 can allow visual inspection and monitoring of the respective drug containers to, for example, monitor delivery progress or status.

In various embodiments, a patient of the drug delivery device 100 can monitor an amount of liquid drug remaining in each drug container. In this way, a patient can monitor dosing status. The windows 110 and 112 can also enable a patient to inspect the liquid drugs for particles or discoloration. The windows 110 and 112 can each be covered with a clear material such as plastic to allow a user to view the contents of each respective drug container. The windows 110 and 112 can be of any size or shape and can be positioned along any portion of the drug delivery device 100.

Many conventional drug delivery devices that can store and deliver relatively large volumes of liquid drugs to a user are generally shaped to be long and thin. Such conventional drug delivery devices are generally not comfortable when worn by the patient. Further, many conventional drug delivery devices that can dispense 10 mL or more of a stored liquid drug are not intended to be worn by the patient. In contrast, the drug delivery device 100 can store and deliver 10 mL or more of one or more liquid drugs to the user while being comfortably worn by the patient. Further, in contrast to many conventional drug delivery devices, the drug delivery device 100 can be filled or refilled by a user.

Figure 2:
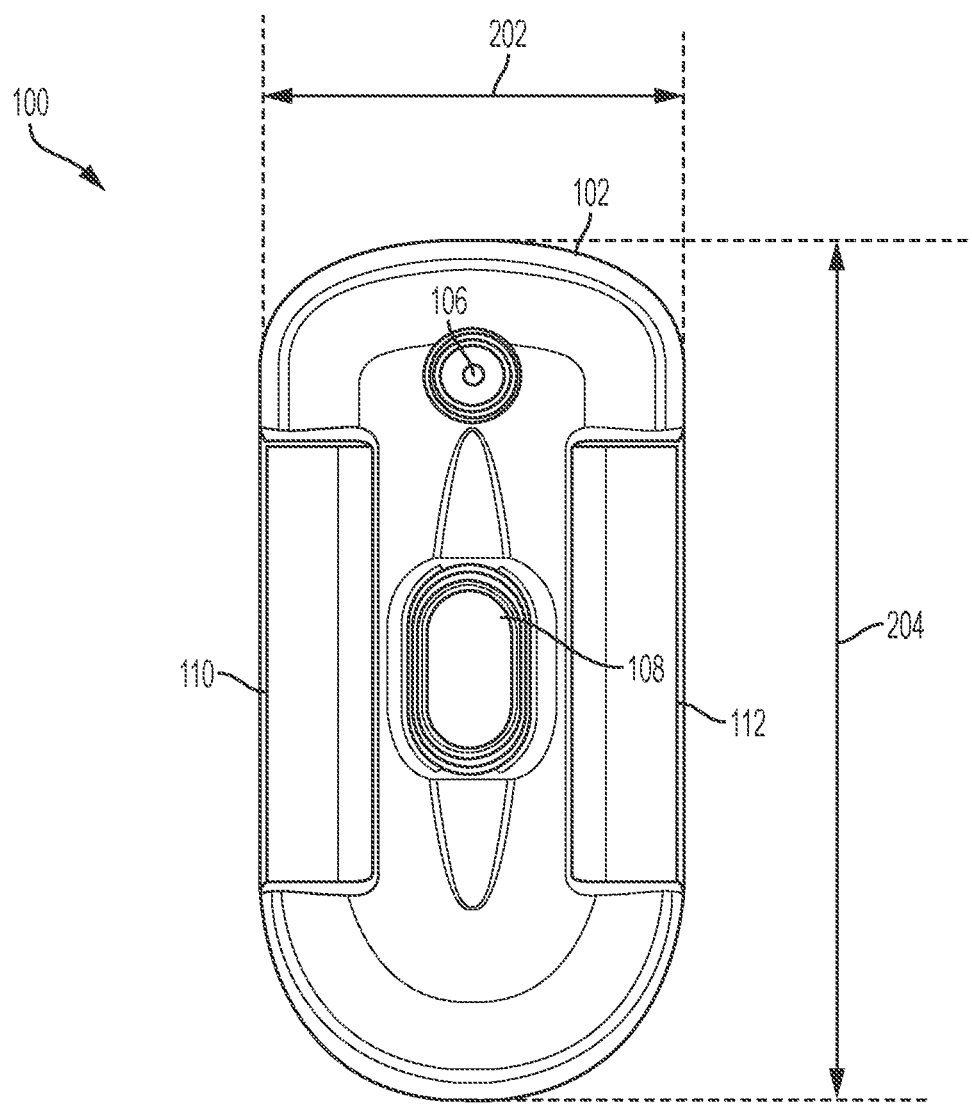
FIG. 2 illustrates a top view of the drug delivery device of FIG. 1.

FIG. 2 illustrates a top view of the drug delivery device 100. As shown in FIG. 2, an exemplary arrangement of the fill port 106, the patient interaction element 108, and the viewing windows 110 and 112 are shown. In various embodiments, the drug delivery device 100 can have a width 202 of approximately 35 mm. In various embodiments, the drug delivery device 100 can have a length 204 of approximately 91 mm. The arrangement of the fill port 106, the patient interaction element 108, and the viewing windows 110 and 112 allows a patient to conveniently monitor the delivery progress of the stored liquid drugs while also being able to control or activate the drug delivery device 100 when the drug delivery device 100 is worn by the user.

Figure 3:
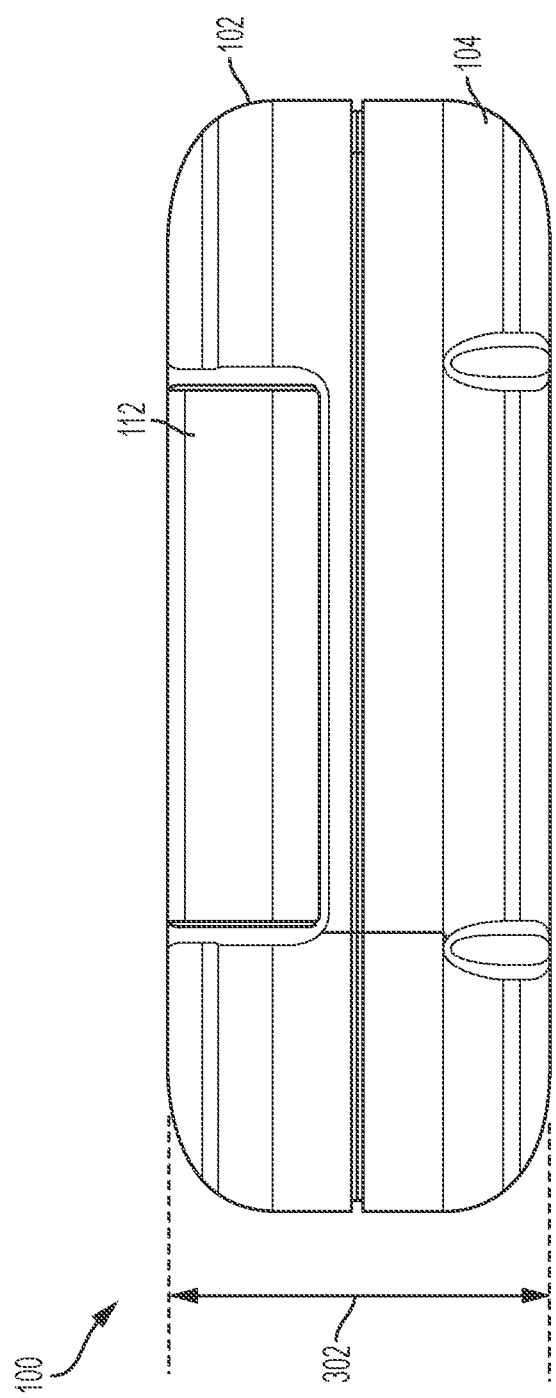
FIG. 3 illustrates a side view of the drug delivery device of FIG. 1.

FIG. 3 illustrates a side view of the drug delivery device 100. As shown in FIG. 3, an exemplary arrangement of the viewing window 112 is shown in relation to the top portion 102 and the lower portion 104 of the drug delivery device 100. In various embodiments, the drug delivery device 100 can have a height 302 of approximately 31 mm.

In various embodiments, the drug delivery device 100 can include a user interface. The user interface can include, for example, a touchscreen, a liquid crystal display (LCD), light emitting diode (LED) display, or any other type of display for presenting information to the patient and/or receiving one or more inputs from the patient. In general, the user interface can include one or more interfaces for displaying or providing information to the patient and/or receiving information from the patient. In various embodiments, the user interface can provide an electronic display indicating the fill and/or dosing status (or any other operational status) of the drug delivery device 100.

In various embodiments, the drug delivery device 100 can include one or more drive mechanisms. In various embodiments, a drive mechanism can be provided for each container that stores, for example, a liquid drug. The drive mechanisms can be of the same type of drive mechanism or can be different drive mechanisms. Each drive mechanism can be used to expel a liquid drug from a corresponding container for delivery to the patient. For example, each drive mechanism can be used to expel a desired amount of a liquid drug that is to be provided to the patient over a certain amount of time. In various embodiments, each drive mechanism can operate to control a plunger that can expel a portion of a liquid drug from a respective container based on the movement of the plunger. In various embodiments, the plunger can be positioned within a drug storage container and can be moved within the container by a corresponding drive mechanism. A variety of drive mechanisms can be used and implemented by the drug delivery device 100 including any of the mechanisms, features, and/or components for storing and delivering a liquid drug from a container to a user as described in U.S. application Ser. No. 15/607,169, filed May 26, 2017, U.S. application Ser. No. 15/607,182, filed May 26, 2017, U.S. Provisional Application No. 62/562,802, filed Sep. 25, 2017, and U.S. Provisional Application No. 62/562,807, filed Sep. 25, 2017, each of which is incorporated by reference in their entirety.

Figure 4:
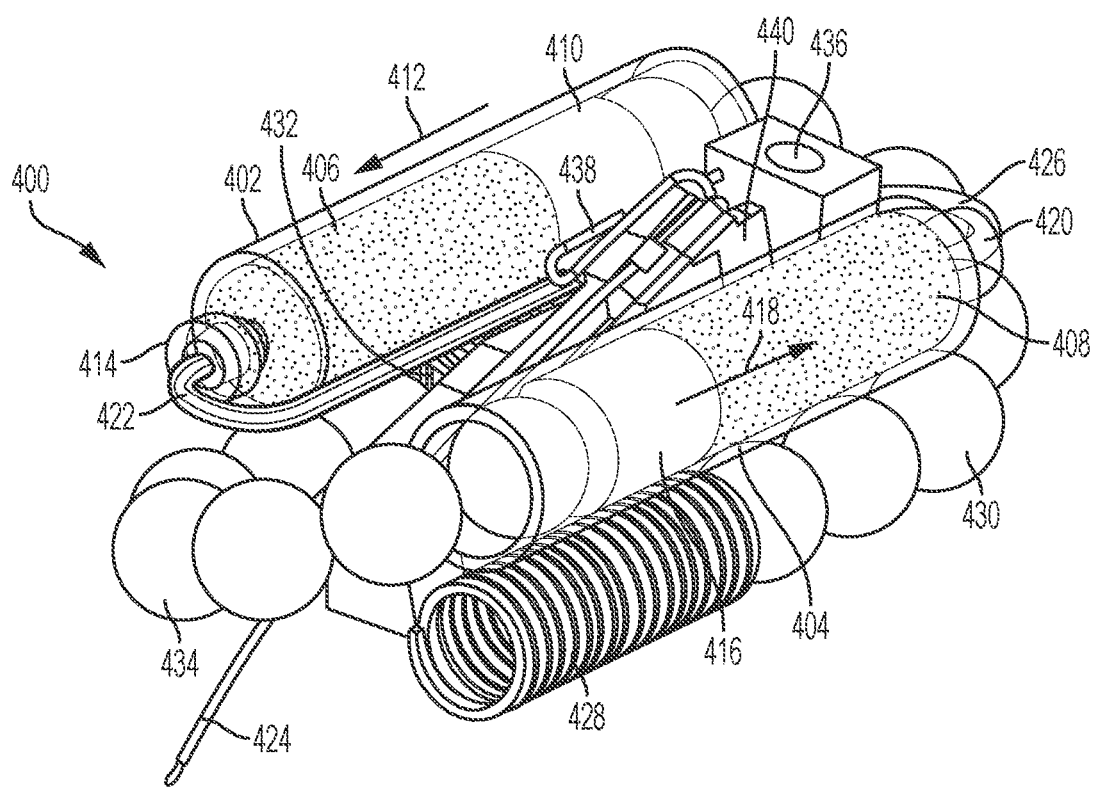
FIG. 4 illustrates a first exemplary arrangement of various internal components of the drug delivery device of FIGS. 1-3.

FIG. 4 illustrates a first exemplary arrangement of various internal components 400 of the drug delivery device 100. The various internal components 400 depicted in FIG. 4 can be used for storing, for example, one or more liquid drugs, expelling the one or more liquid drugs from respective containers, and for delivering the expelled liquid drugs to a user. The drug delivery device 100 can include additional components other than those depicted in FIG. 4.

As shown in FIG. 4, the internal components 400 can include a first container 402 and a second container 404. As described herein, the first and second containers 402 and 404 can be ISO cartridges. In various embodiments, the first and second containers 402 and 404 can each be 5 mL cartridges and can be of the same size and shape. The first container 402 can hold or store a first liquid drug 406. The second container 404 can hold or store a second liquid drug 408. The first and second liquid drugs 406 and 408 can be the same liquid drug or can be different liquid drugs.

A first plunger 410 can be positioned within the first container 402. The first plunger 410 can be advanced in a direction 412 to expel the first liquid drug 406 from the first container 402. The first liquid drug 406 can be expelled from a first end 414 of the first container 402 based on advancement of the first plunger 410 toward the first end 414. Similarly, a second plunger 416 can be positioned within the second container 404. The second plunger 416 can be advanced in a direction 418 to expel the second liquid drug 408 from the second container 404. The second liquid drug 408 can be expelled from a first end 420 of the second container 404 based on advancement of the second plunger 416 toward the first end 420.

The first end 414 of the first container 402 can be coupled to a first fluid path or tubing component 422. The first tubing component 422 can be coupled to a needle component 424. The needle component 424 can be coupled to the user when it is desired to deliver a stored liquid drug to the user. When the first plunger 410 is advanced in the direction 412, then a portion of the first liquid drug 406 can be expelled from the first container 402 for delivery to the user by way of the first tubing component 422 and the needle component 424. The first end 420 of the second container 404 can be coupled to a second fluid path or tubing component 426. The second tubing component 426 can also be coupled to the needle component 424. When the second plunger 416 is advanced in the direction 418, then a portion of the second liquid drug 408 can be expelled from the second container 404 for delivery to the user by way of the second tubing component 426 and the needle component 424. The needle component 424 can be supported by and/or coupled to a structural component 440.

The first plunger 410 can be moved by operation of a first spring 428 and first energy transfer spheres 430 (or a first set of energy transfer spheres). The first spring 428 can be a compression spring and can be coupled to the first energy transfer spheres 430. The first energy transfer spheres 430 can be coupled to the first plunger 410. The first energy transfer spheres 430 can include any number of spheres. The first spring 428 can be positioned below the second container 404. A track or other guide not shown in FIG. 4 can be used to guide the energy transfer spheres 430 to provide coupling between the first spring 428 and the first plunger 410. When the first spring 428 is released and expands, the first spring 428 can provide a force to advance the energy transfer spheres 430 toward the first plunger 410. The force provided by the first spring 428 can be transferred to the first plunger 410 by way of the energy transfer spheres 430, thereby causing the first plunger 410 to advance in the direction 412. The energy transfer spheres 430 can be sized to enter an open end of the first container 402 to advance the first plunger 410 further into the first container 402 (e.g., toward the first end 414).

In a similar manner, the second plunger 416 can be moved by operation of a second spring 432 and second energy transfer spheres 434 (or a second set of energy transfer spheres). The second spring 432 can be a compression spring and can be coupled to the second energy transfer spheres 434. The second energy transfer spheres 434 can be coupled to the second plunger 416. The second energy transfer spheres 434 can include any number of spheres. The second spring 432 can be positioned below the first container 402. A track or other guide not shown in FIG. 4 can be used to guide the second energy transfer spheres 434 to provide coupling between the second spring 432 and the second plunger 416. When the second spring 432 is released, the second spring 432 can provide a force to advance the second energy transfer spheres 434 toward the second plunger 416. The force provided by the second spring 432 can be transferred to the second plunger 416 by way of the second energy transfer spheres 434, thereby causing the second plunger 432 to advance in the direction 418. As shown in FIG. 4, the directions 412 and 418 can be approximately opposite. The energy transfer spheres 434 can be sized to enter an open end of the second container 404 to advance the second plunger 416 further into the second container 404 (e.g., toward the first end 420).

A fill port component 436 can be used to access the first and second containers 402 and 404. In various embodiments, the fill port component 436 can include an opening that can be aligned with the fill port 106 as shown in FIGS. 1 and 2. The fill port component 436 can be coupled to the first tubing component 422 and the second tubing component 426. The fill port component 436 can enable the user to fill the first container 402 with the first liquid drug 406 through the first tubing component 422 and to fill the second container 404 with the second liquid drug 408 through the second tubing component 426. The fill port component 436 can include one or more valves for directing fluid provided by the user to either the first container 402 or the second container 404 such that the first container 402 can be filled with the first liquid drug 406 and the second container 404 can be filled with the second liquid drug 408.

The fill port component 436 can also be coupled to the needle component 424. A tubing component 438 can provide connectivity between the fill port component 436 and the needle component 424. When expelling the liquid drugs 406 and 408, the tubing components 422 and 426 can provide connectivity to the fill port component 436 which can then provide the expelled liquid drugs 406 and 408 to the needle component 424 through the tubing component 438. As described herein, one or more valves of the fill port component 436 can direct the flow of the first and second liquid drugs 406 and 408 into the first and second containers 402 and 404, respectively, or from the first and second containers 402 and 404 to the needle component 424.

The first spring 428 and the energy transfer spheres 430 can form a portion of a first drive mechanism of the drug delivery device 100. This first drive mechanism, as described herein, can be used to deliver the stored first liquid drug 406 to the user. The second spring 432 and the energy transfer spheres 434 can form a portion of a second drive mechanism of the drug delivery device 100. This second drive mechanism, as described herein, can be used to deliver the stored second liquid drug 408 to the user.

The arrangement of the internal components of the drug delivery device 100 shown in FIG. 4 allows the drug delivery device 100 to remain relatively small, compact, and lightweight. As a result, the drug delivery device 100 can have a size and shape (e.g., as shown in FIGS. 1-3) that can be comfortable for a user to wear.

Figure 5:
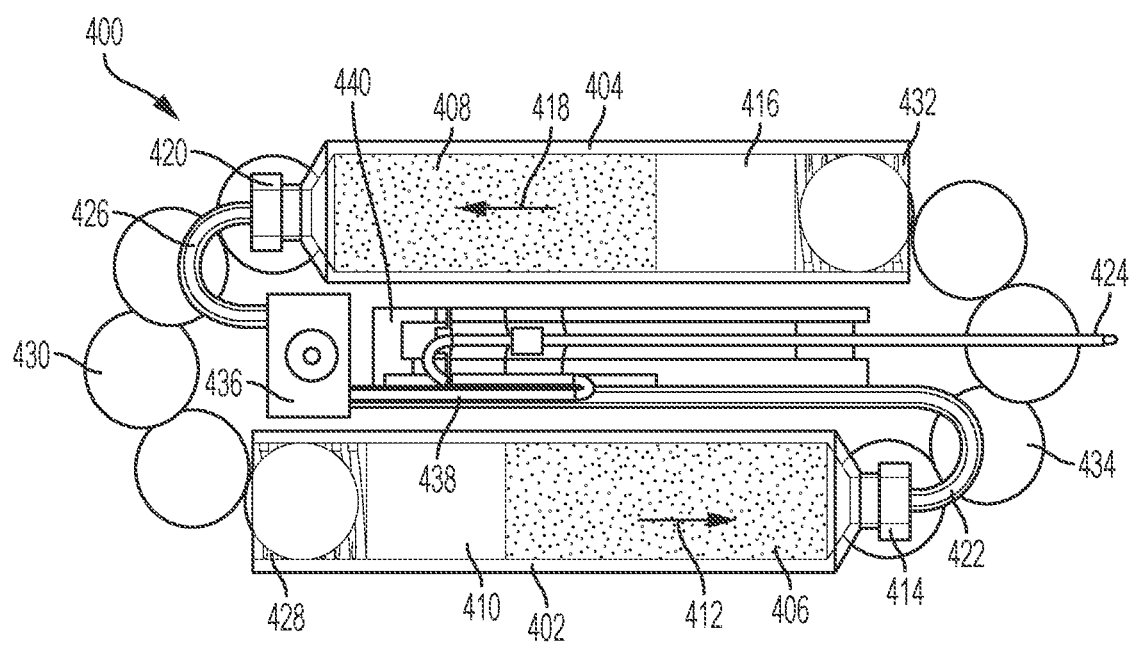
FIG. 5 illustrates a top view of the internal components depicted in FIG. 4.

FIG. 5 illustrates a top (or overhead) view of the internal components 400 of the drug delivery device 100 shown in FIG. 4. The tubing components 422, 426, and 438 can each be flexible tubing comprising any suitable material including plastic or stainless steel. The tubing component 422 and tubing component 426 can have the same inner diameters (e.g., to maintain the same flow rate capabilities from the first and second containers 402 and 404, respectively) or can have different inner diameters.

As shown in FIG. 5, the first container 402 is oriented in an approximately opposite direction from an orientation of the second container 404. Specifically, the first end 420 of the second container 404 is located adjacent to and proximate to the fill port component 436 while the first end 414 of the first container 402 is located distal to the fill port component 436. The first end 414 of the first container 402 can be positioned closer to a tip or end of the needle component 424 (e.g., a tip or end of the needle component 424 coupled to the user). As shown in FIG. 5, the first end 414 of the first container 402 is adjacent to an open end of the second container 404 that enables the energy transfer spheres 434 to enter the second container 404. The first end 420 of the second container 404 is adjacent to an open end of the first container 402 that enables the energy transfer spheres 4340 to enter the first container 402.

Figure 6:
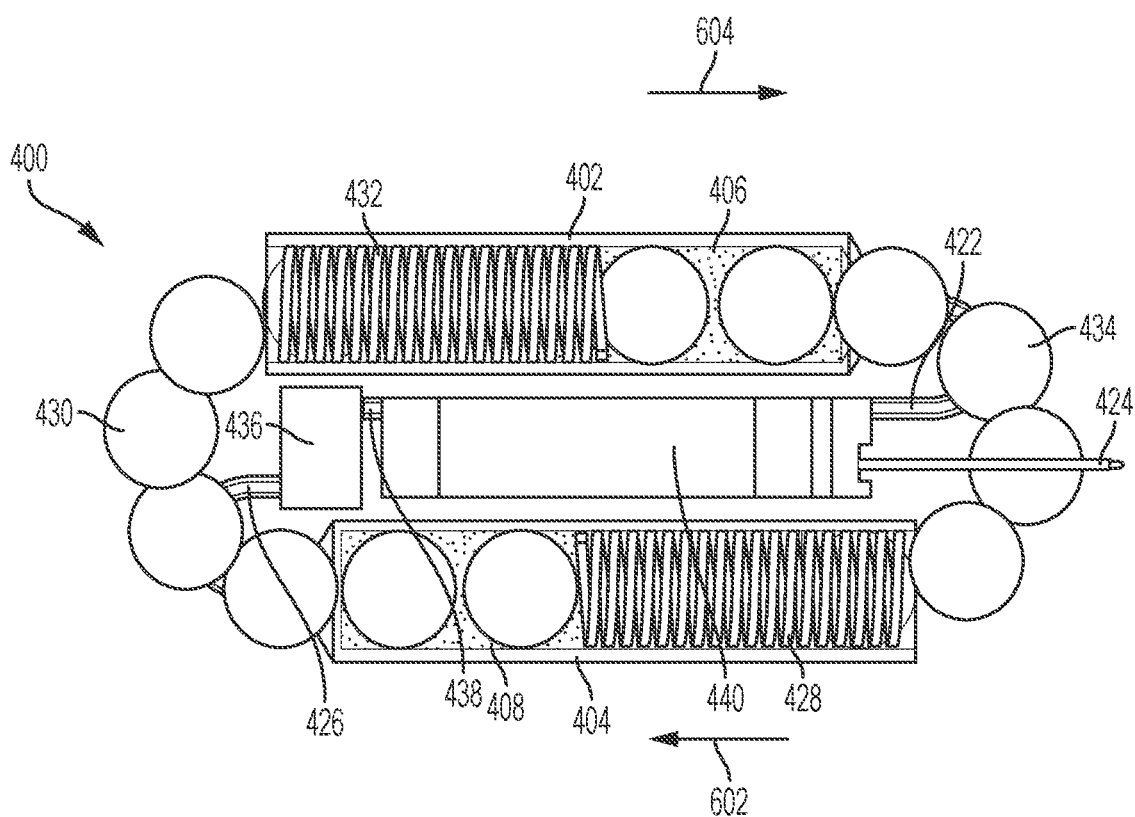
FIG. 6 illustrates a bottom view of the internal components depicted in FIG. 4.

FIG. 6 illustrates a bottom (or underside) view of the internal components 400 of the drug delivery device 100 as shown in FIG. 4. FIGS. 5 and 6 together illustrate the compact arrangement of the internal components 400 including exemplary positioning of the first spring 428 under the second container 404 and the exemplary positioning of the second spring 432 under the first container 402. Further, the energy transfer spheres 430 are shown wrapped around a first end of the arrangement depicted in FIG. 6 and the energy transfer spheres 434 are shown wrapped around a second, opposite end. The arrangement of the internal components 400 as shown in FIGS. 4-6 enables the overall height of the internal components 400 to be relatively low while maintaining a manageable length of the drug delivery device 100, thereby providing a comfortable experience by the user when the drug delivery device 100 is worn.

As shown in FIG. 6, a first indicator 602 represents an applied force from the first spring 428 (or a direction of an applied force from the first spring 428). The applied force from the first spring 428 is transferred by the energy transfer spheres 430 to the first plunger 410 (not shown in FIG. 6) of the first container 402. The expansion of the first spring 428 in the direction 602 advances the energy transfer spheres 430 toward the first container 402. Similarly, a second indicator 604 represents an applied force from the second spring 432 (or a direction of an applied force from the second spring 432). The applied force from the second spring 432 is transferred by the energy transfer spheres 434 to the second plunger 416 (not shown in FIG. 6) of the second container 404. The expansion of the second spring 432 advances the energy transfer spheres 434 and, consequently, the second plunger 416.

Figure 7:
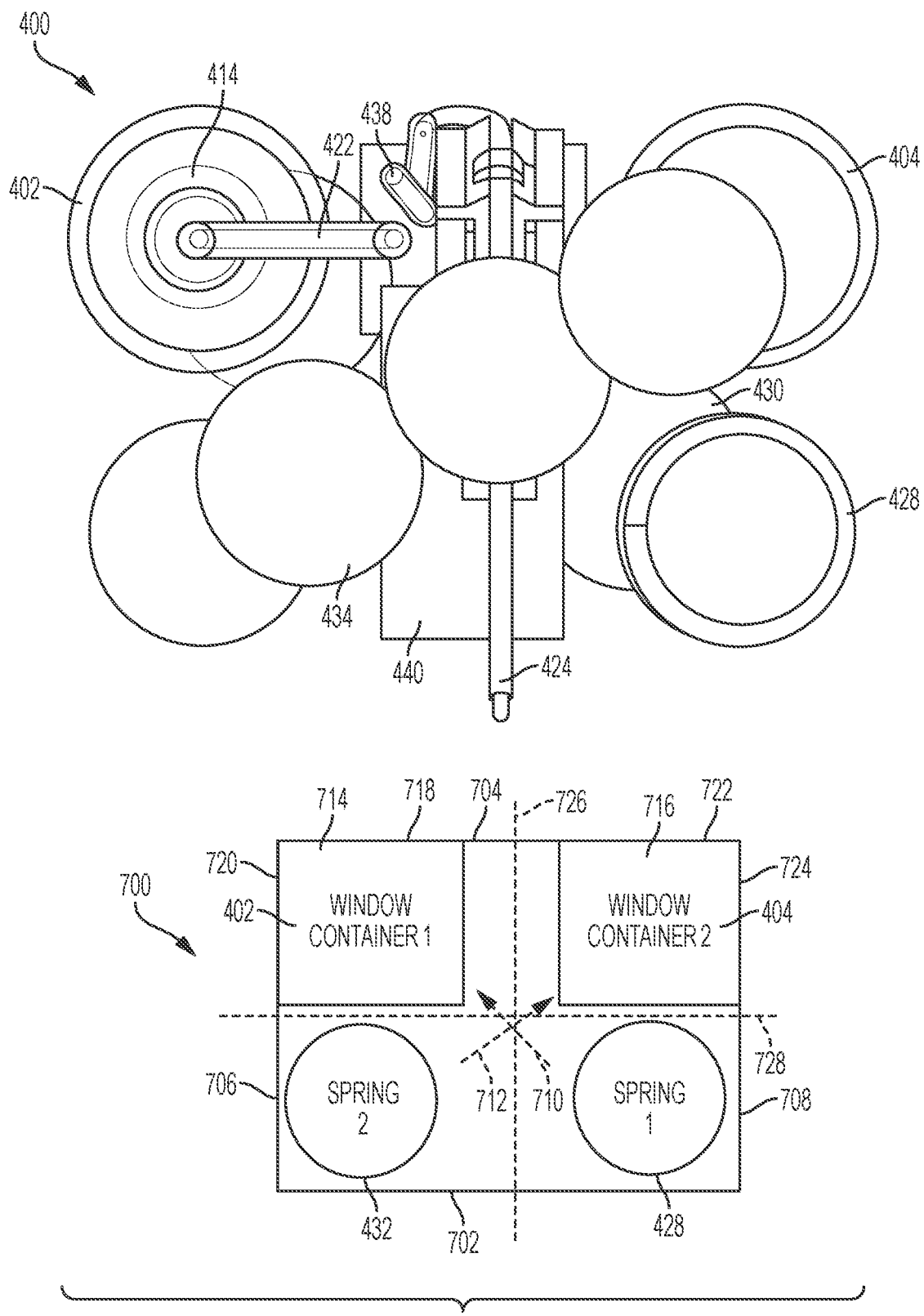
FIG. 7 illustrates a front view of the internal components depicted in FIG. 4.

FIG. 7 illustrates a front (or head-on) view of the exemplary arrangement of the various internal components 400 of the drug delivery device 100 as well as a block diagram 700 representing the exemplary arrangement of the various internal components 400. Specifically, FIG. 7 illustrates a view of the exemplary arrangement of the various internal components 400 when facing the needle component 424 and the energy transfer spheres 434 relative to the depictions of the internal components 400 in FIGS. 4-6. Further, the block diagram 700 of FIG. 7 functionally represents the internal components 400 in a simplified manner to highlight the exemplary arrangement of the internal components 400 depicted in FIGS. 4-6.

As shown in FIG. 7, the block diagram 700 represents the drug delivery device 100 when it incorporates the internal components 400 as arranged in FIGS. 4-6. A bottom surface 702, a top surface 704, a first side surface 706, and a second side surface 708 represent the housing and/or outer surfaces of the drug delivery device 100. The first and second springs 428 and 432 are positioned adjacent to the bottom surface 702. The first and second containers 402 and 404 are positioned adjacent to the top surface 704. The first spring 428 is positioned under the second container 404 and the second spring 432 is positioned under the first container 402.

Indicator 710 represents the application of a force (or direction or path of a force) from the first spring 428 (e.g., via energy transfer spheres 430) to expel a liquid drug (e.g., the liquid drug 406) from the first container 402. Indicator 712 represents the application of a force (or direction or path of a force) from the second spring 432 (e.g., via energy transfer spheres 434) to expel a liquid drug (e.g., the liquid drug 408) from the second container 404. As shown, the drive mechanism associated with the first container 402—which can include the first spring 428 and the energy transfer spheres 430—crosses the drive mechanism associated with the second container 402—which can include the second spring 432 and the energy transfer spheres 434. This arrangement provides a suitable path for the energy transfer spheres 430 and 434 that is not too tight or narrow while still providing a compact arrangement of the internal components 400.

FIG. 7 further illustrates exemplary positioning of windows or openings 714 and 716 for viewing the first and second containers 402 and 404, respectively. In particular, the window 714 can be used to view a portion of the first container 402. The window 714 can be arranged to occupy a portion 718 of the top surface 704 and/or a portion 720 of the side surface 706. The window 716 can be arranged to occupy a portion 722 of the top surface 704 and/or a portion 724 of the side surface 708.

For reference, the block diagram 700 includes a first central axis (or plane) 726 and a second central axis (or plane) 728. Relative to the depiction of the internal components 400 as arranged in FIG. 7, the first axis 726 divides the block diagram 700 between a right side and a left side. The right side can include the first spring 428 and the second container 404. The left side can include the second spring 432 and the first container 402.

Relative to the depiction of the internal components 400 as arranged in FIG. 7, the second axis 728 divides the block diagram 700 between a top portion and a bottom portion. The top portion can include the first and second containers 402 and 404. The bottom portion can include the first and second springs 428 and 432. As shown, indicator 710 traverses or crosses the first and second axes 726 and 728—accordingly, the first spring 428 operates on the first container 402 by applying a force through the energy transfer spheres 430 that traverses both the first and second axes 726 and 728. Similarly, indicator 712 traverses or crosses the first and second axes 726 and 728—accordingly, the second spring 432 operates on the second container 404 by applying a force through the energy transfer spheres 434 that traverses both the first and second axes 726 and 728.

As shown in FIGS. 4-7, the first container 402 can be oriented in an opposite direction relative to an orientation of the second container 404. Specifically, the first end 420 of the second container 404 can be positioned closer to the fill port component 436 while the first end 414 of the first container 402 can be positioned further from the fill port component 436. As such, the first plunger 410 can be moved in the direction 412 to expel the first liquid drug 406 that is approximately opposite to the direction 418 that the plunger 416 is moved to expel the second liquid drug 408. As shown in FIG. 6, the direction 602 of expansion of the first spring 428 can be approximately opposite to the direction 604 of expansion of the second spring 432. The direction 602 can be approximately opposite to the direction 412 of the first plunger 410 while the direction 604 can be approximately opposite to the direction 418 of the second plunger 416.

The drug delivery device 100 can be operated to expel and deliver the first liquid drug 406 to the user before subsequently expelling and delivering the second liquid drug 408 to the user. In various embodiments, the first liquid drug 406 and the second liquid drug 408 can be mixed and delivered to the user in any combination. Any ratio of mixing the first and second liquid drugs 406 and 408 can be provided. The ratio of mixing can be based on the amount of the first and second liquid drugs 406 and 408 stored in the first and second containers 402 and 404, respectively (e.g., a fill ratio between the first and second containers 402 and 404). In various embodiments, the ratio of mixing can be based on rates of expelling the first and second liquid drugs 406 and 408 from the first and second containers 402 and 404, respectively. In various embodiments, the drug delivery device 100 can be used to reconstitute one or more drugs for delivery to the user.

Figure 8:
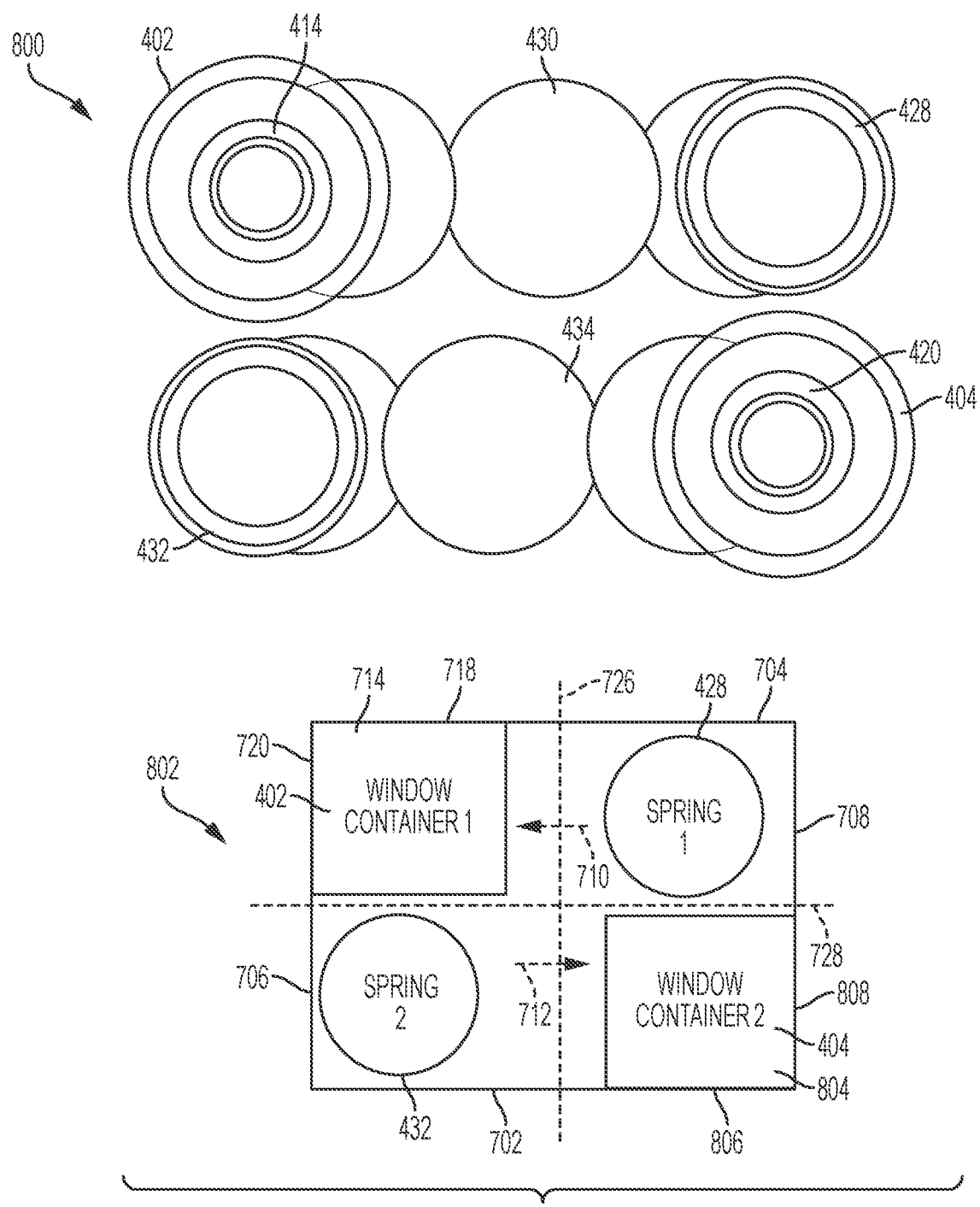
FIG. 8 illustrates a front view of a first alternative arrangement of internal components of the drug delivery device of FIGS. 1-3.

FIG. 8 illustrates a front view of a first alternative arrangement of various internal components 800 of the drug delivery device 100 as well as a block diagram 802 representing the exemplary arrangement of the various internal components 800. The block diagram 802 of FIG. 8 functionally represents the internal components 800 in a simplified manner to highlight the exemplary arrangement of the internal components 800. Various additional components are not shown for simplicity (e.g., the needle component 424) to better illustrate the exemplary arrangement of storage containers and drive mechanisms.

As shown in FIG. 8, the block diagram 802 represents the drug delivery device 100 when it incorporates the internal components 800. The first spring 428 and the first container 402 are positioned adjacent to the top surface 704. The second spring 432 and the second container 404 are positioned adjacent to the bottom surface 702. The second spring 432 is positioned under the first container 402 and the second container 404 is positioned under the first spring 428. The first and second containers 402 and 404 can be oriented in the same direction (e.g., the first and second plungers 410 and 416 can be moved in the same direction to expel the first and second liquid drugs 406 and 408, respectively). The first and second springs 428 and 432 can also be oriented in the same direction (e.g., the first and second springs 428 and 432 can extend in the same direction to advance forward the first and second sets of energy transfer spheres 430 and 434, respectively).

The application of a force from the first spring 428 (e.g., via the energy transfer spheres 430) to expel a liquid drug (e.g., the liquid drug 406) from the first container 402 is represented by indicator 710, which is positioned above central axis 728, and traverses or crosses central axis 726. The application of a force from the second spring 432 (e.g., via the energy transfer spheres 434) to expel a liquid drug (e.g., the liquid drug 408) from the second container 404 is represented by indicator 712, which is positioned below central axis 728, and traverses or crosses central axis 726. As shown, indicators 710 and 712 represent applied forces (or directions or paths of applied forces) that are applied in approximately opposite directions. This arrangement provides a suitable path for the energy transfer spheres 430 and 434 that is not too tight or narrow while still providing a compact arrangement of the internal components 800.

FIG. 8 further illustrates exemplary positioning of windows or openings 714 and 804 for viewing the first and second containers 402 and 404, respectively. In particular, the window 714 can be used to view a portion of the first container 402. The window 714 can be arranged to occupy a portion 718 of the top surface 704 and/or a portion 720 of the side surface 706. The window 804 can be arranged to occupy a portion 806 of the bottom surface 702 and/or a portion 808 of the side surface 708. Relative to the first and second central axes 726 and 728, the right side of the block diagram 902 can include the first spring 428 and the second container 404. The left side of the block diagram 902 can include the second spring 432 and the first container 402.

Figure 9:
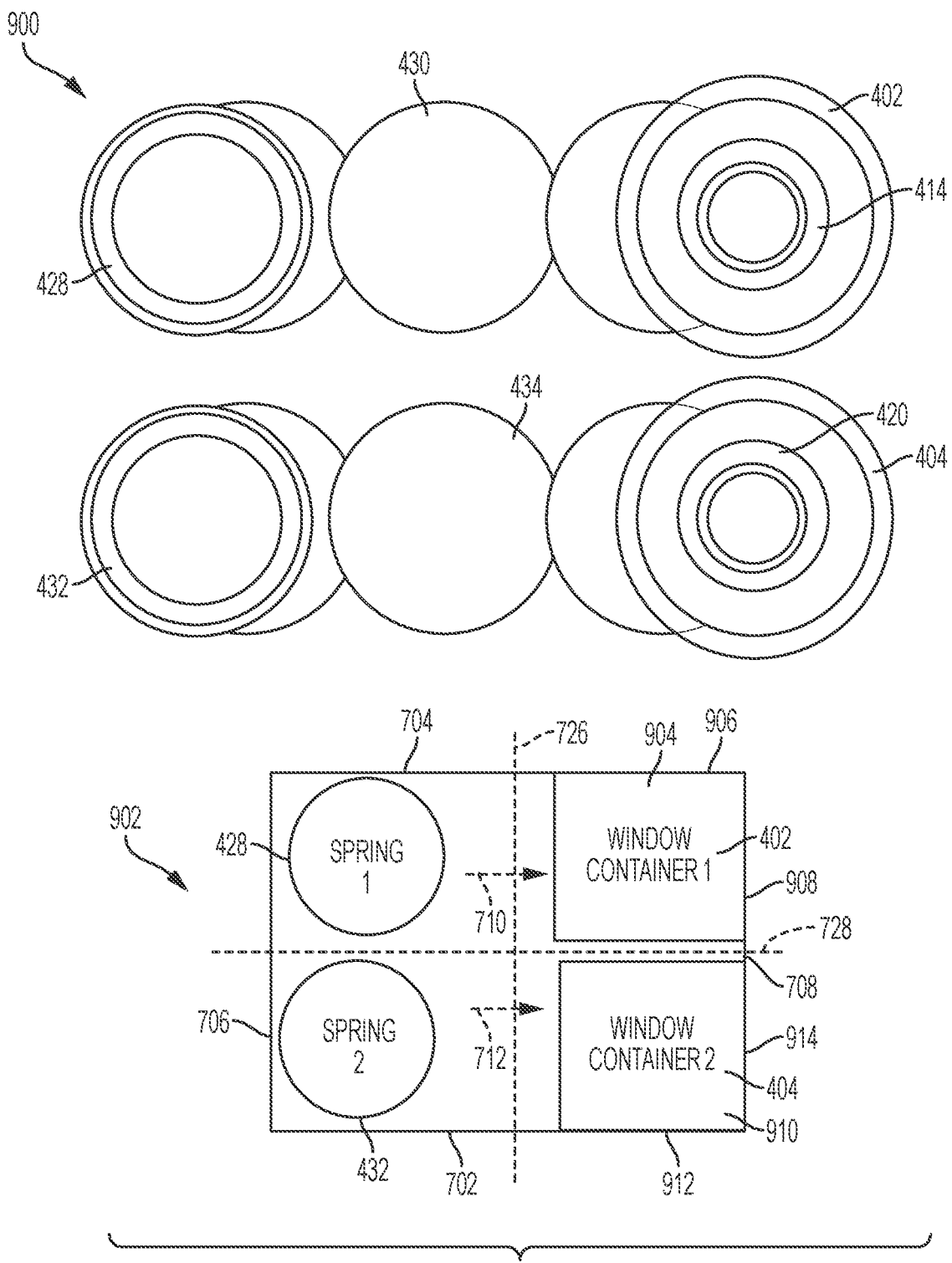
FIG. 9 illustrates a front view of a second alternative arrangement of internal components of the drug delivery device of FIGS. 1-3.

FIG. 9 illustrates a front view of a second alternative arrangement of various internal components 900 of the drug delivery device 100 as well as a block diagram 902 representing the exemplary arrangement of the various internal components 900. The block diagram 902 of FIG. 9 functionally represents the internal components 900 in a simplified manner to highlight the exemplary arrangement of the internal components 900. Further, various components are not shown for simplicity (e.g., the needle component 424) to better illustrate the exemplary arrangement of storage containers and drive mechanisms.

As shown in FIG. 9, the block diagram 902 represents the drug delivery device 100 when it incorporates the internal components 900. The first spring 428 and the first container 402 are positioned adjacent to the top surface 704. The second spring 432 and the second container 404 are positioned adjacent to the bottom surface 702. The second spring 432 is positioned under the first spring 428 and the second container 404 is positioned under the first container 402. The first and second containers 402 and 404 can be oriented in the same direction. The first and second springs 428 and 432 can also be oriented in the same direction.

The application of a force from the first spring 428 (e.g., via the energy transfer spheres 430) to expel a liquid drug (e.g., the liquid drug 406) from the first container 402 is represented by indicator 710, which is positioned above central axis 728 and traverses or crosses central axis 726. The application of a force from the second spring 432 (e.g., via the energy transfer spheres 434) to expel a liquid drug (e.g., the liquid drug 408) from the second container 404 is represented by indicator 712, which is positioned below central axis 728 and traverses or crosses central axis 726. As shown, indicators 710 and 712 represent applied forces (or directions or paths of applied forces) that are applied in the same direction. This arrangement provides a suitable path for the energy transfer spheres 430 and 434 that is not too tight or narrow while still providing a compact arrangement of the internal components 900.

FIG. 9 further illustrates exemplary positioning of windows or openings 904 and 910 for viewing the first and second containers 402 and 404, respectively. In particular, the window 904 can be used to view a portion of the first container 402. The window 904 can be arranged to occupy a portion 906 of the top surface 704 and/or a portion 908 of the side surface 708. The window 910 can be arranged to occupy a portion 912 of the bottom surface 702 and/or a portion 914 of the side surface 708. Relative to the first and second central axes 726 and 728, the right side of the block diagram 902 can include the first container 402 and the second container 404. The left side of the block diagram 902 can include the first spring 428 and the second spring 432.

Various embodiments described herein—including, for example the various exemplary arrangements of internal components 400, 800, and 900 depicted in FIGS. 7-9—enable relatively large volumes of one or more drugs (e.g., 10 mL or more) to be delivered to the user. Various embodiments described herein can store the one or more drugs across two or more containers. By using more than one container, a stroke of any spring (or other delivery mechanism) used to expel the liquid drugs from their respective containers can be shorter than the stroke of any spring (or other delivery mechanism) used in conventional drug delivery devices that are used for high volume drug delivery. As a result, an efficiency of the drive mechanism used for delivery of the liquid drugs within the embodiments described herein can be improved over conventional devices. Further, as described herein, the arrangement of the internal components 400, 800, and 900 enables the drug delivery device 100 to made in a compact form to improve the comfort of a user that wears the drug delivery device 100. In particular, the arrangement of components as shown in at least FIGS. 7-9 enable the internal components for storing and delivering large volumes of one or more drugs to be arranged in a highly efficient manner that is compact, allowing the wearable drug delivery device to remain small and comfortable to wear.

For the sake of convenience and clarity, terms such as "front," "rear," "outer," "inner," "top," "bottom," "upper," "lower," "upwards," "downwards," "vertical," "horizontal," "lateral," "longitudinal," "height," "above," "below," "top," "bottom," "left," "right," and "width" (and/or other related terms including those specifically mention, derivatives thereof, and terms of similar import) may have been used herein to describe the relative placement and orientation of the device and/or its various components, each with respect to the geometry and orientation of the device and/or its components as they appear in the figures, and is not intended to be limiting.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A wearable drug delivery device, comprising:
a first container configured to store a first liquid drug;
a second container configured to store a second liquid drug, wherein the first container and the second container are positioned along a first plane;
a first spring;
a second spring, wherein the first spring and the second spring are positioned along a second plane, the second plane extending parallel to the first plane;
a first set of energy transfer spheres coupled to the first spring and a first plunger positioned within the first container, wherein the first set of energy transfer spheres extends between the second plane and the first plane;
a second set of energy transfer spheres coupled to the second spring and a second plunger positioned within the second container, wherein the second set of energy transfer spheres extends between the second plane and the first plane; and
a needle component coupled to the first and second containers, wherein the first set of energy transfer spheres extends across a central axis extending along a length of the needle component, the central axis defining a third plane oriented perpendicular to the first and second planes.

2. The wearable drug delivery device of claim 1, wherein the first spring is configured to expand in a first direction to advance the first set of energy transfer spheres toward the first plunger and to advance the first plunger further into the first container, wherein advancing the first plunger further into the first container is configured to expel a portion of the first liquid drug from the first container for delivery to a user.

3. The wearable drug delivery device of claim 2, wherein the second spring is configured to expand in a second direction to advance the second set of energy transfer spheres toward the second plunger and to advance the second plunger further into the second container, wherein advancing the second plunger further into the second container is configured to expel a portion of the second liquid drug from the second container for delivery to the user.

4. The wearable drug delivery device of claim 3, wherein the first and second directions are approximately opposite directions.

5. The wearable drug delivery device of claim 4, wherein the first plunger is configured to be advanced in the second direction when the first spring expands in the first direction.

6. The wearable drug delivery device of claim 5, wherein the second plunger is configured to be advanced in the first direction when the second spring expands in the second direction.

7. The wearable drug delivery device of claim 6, wherein the portion of the first liquid drug is expelled from the first container in the second direction and the portion of the second liquid drug is expelled from the second container in the first direction.

8. The wearable drug delivery device of claim 3, wherein the wearable drug delivery device is configured to expel the second liquid drug from the second container after the first liquid drug from the first container is expelled.

9. The wearable drug delivery device of claim 3, wherein the wearable drug delivery device is configured to expel the first and second liquid drugs at substantially the same time.

10. The wearable drug delivery device of claim 9, wherein the first and second liquid drugs are mixed prior to delivery to the user.

11. The wearable drug delivery device of claim 1, wherein the first and second liquid drugs are a same type of liquid drug.

12. The wearable drug delivery device of claim 1, wherein the first and second liquid drugs are different types of liquid drugs.

13. The wearable drug delivery device of claim 1, wherein the first container and the second container are each 5 mL cartridges.

14. The wearable drug delivery device of claim 1, wherein the first and second springs are each compression springs.

15. The wearable drug delivery device of claim 1, wherein the first and second sets of energy transfer spheres each comprise two or more energy transfer spheres.

16. The wearable drug delivery device of claim 15, wherein the first and second sets of energy transfer spheres each comprise the same number of energy transfer spheres.

17. The wearable drug delivery device of claim 1, wherein the needle component is configured to couple the wearable drug delivery device to a user upon activation of the wearable drug delivery device by the user.

18. The wearable drug delivery device of claim 1, wherein the first spring is positioned under the second container.

19. The wearable drug delivery device of claim 18, wherein the second spring is positioned under the first container.

20. The wearable drug delivery device of claim 19, further comprising a fill port coupled to the first and second containers, the fill port configured to enable a user to fill the first container with the first liquid drug and to fill the second container with the second liquid drug.

* * * * *